United States Patent [19]

Albertson

[11] 4,022,789

[45] May 10, 1977

[54] DICHLOROCYCLOPROPYLMETHYL-BENZAZOCINES

[75] Inventor: Noel F. Albertson, Schodack, N.Y.

[73] Assignee: Sterling Drug Inc., New York, N.Y.

[22] Filed: Nov. 20, 1975

[21] Appl. No.: 633,830

[52] U.S. Cl. .................. 260/293.54; 260/DIG. 13; 424/267

[51] Int. Cl.² ..................................... C07D 221/26

[58] Field of Search ................ 260/293.54, DIG. 13

[56] References Cited

UNITED STATES PATENTS

| | | | |
|---|---|---|---|
| 3,372,165 | 3/1968 | Archer | 260/294.7 |
| 3,514,463 | 5/1970 | Robinson et al. | 260/294.7 |
| 3,639,407 | 2/1972 | Clarke et al. | 260/293.54 |
| 3,700,734 | 10/1972 | Robinson et al. | 260/293.54 |
| 3,957,793 | 5/1976 | Wentland et al. | 260/293.54 |

*Primary Examiner*—G. Thomas Todd
*Attorney, Agent, or Firm*—Theodore C. Miller; B. Woodrow Wyatt

[57] ABSTRACT

6-X-11-Y-3-(2,2-Dichlorocyclopropyl)methyl-1,2,3,4,5,6-hexahydro-2,6-methano-3-benzazocin-8-ols wherein X is hydrogen, methyl, ethyl, propyl, allyl or phenyl and Y is hydrogen, methyl or ethyl, are prepared by N-alkylation, N-acylation-reduction or O-demethylation and are useful as strong analgesics and narcotic antagonists.

2 Claims, No Drawings

DICHLOROCYCLOPROPYLMETHYL-BENZAZOCINES

BACKGROUND OF THE INVENTION

1. Field of the Invention

This invention relates to 1,2,3,4,5,6-hexahydro-8-hydroxy-2,6-methano-3-benzazocines, also known as 6,7-benzomorphans.

2. Description of the Prior Art

3-Cyclopropylmethyl-1,2,3,4,5,6-hexahydro-2,6-methano-3-benzazocin-8-ols are described by U.S. Pat. No. 3,372,165.

SUMMARY OF THE INVENTION

In a composition of matter aspect the invention is 6-X-11-Y-3-(2,2-dichlorocyclopropyl)methyl-1,2,3,4,5,6-hexahydro-2,6-methano-3-benzazocin-8-ol having the structural formula

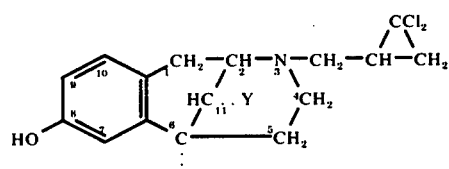

Formula I wherein
X is hydrogen, methyl, ethyl, propyl, allyl or phenyl and Y is hydrogen, methyl or ethyl or an acid addition salt thereof.

The compounds of Formula I are useful as strong analgesics and narcotic antagonists.

In one process aspect the invention is the process for preparing 6-X-11-Y-3-(2,2-dichlorocyclopropyl)methyl-1,2,3,4,5,6-hexahydro-2,6-methano-3-benzazocin-8-ol of Formula I which comprises N-alkylating 6-X-11-Y-1,2,3,4,5,6-hexahydro-2,6-methano-3-benzazocin-8-ol having the structural formula

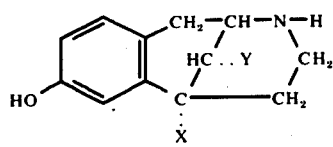

Formula II with (2,2-dichlorocyclopropyl)methyl-An in the presence of an acid absorber wherein X and Y of Formula II are identical with X and Y of Formula I and -An is the anion of a strong organic or inorganic acid.

In another process aspect the invention is the process for preparing 6-X-11-Y-3-(2,2-dichlorocyclopropyl)methyl-1,2,3,4,5,6-hexahydro-2,6-methano-3-benzazocin-8-ol of Formula I which comprises reducing 6-X-11-Y-3-(2,2-dichlorocyclopropyl)carbonyl-1,2,3,4,5,6-hexahydro-8-ZO-2,6-methano-3-benzazocine having the structural formula

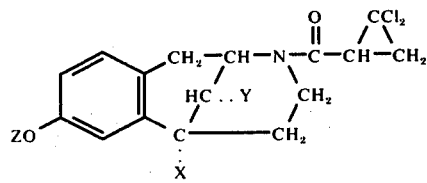

Formula III with a reagent effective in reducing N-carbonyl to N-methylene and in cleaving the (2,2-dichlorocyclopropyl)carbonyl-oxygen bond without affecting any other part of the molecule wherein X and Y of Formula III are identical with X and Y of Formula I and Z is hydrogen or (2,2-dichlorocyclopropyl)carbonyl.

In still another process aspect the invention is the process for preparing 6-X11-Y-3-(2,2-dichlorocyclopropyl)methyl-1,2,3,4,5,6-hexahydro-2,6-methano-3-benzazocin-8-ol of Formula I which comprises O-demethylating 6-X-11-Y-3-(2,2-dichlorocyclopropyl)methyl-1,2,3,4,5,6-hexahydro-8-methoxy-2,6-methano-3-benzazocine having the structural formula

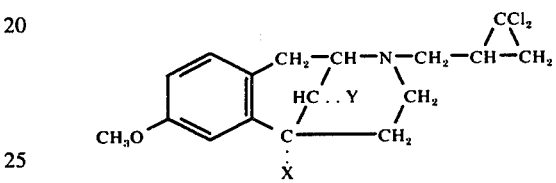

Formula IV with a reagent effective in cleaving the methyl ether bond without affecting any other part of the molecule wherein X and Y of Formula IV are identical with X and Y of Formula I.

DETAILED DESCRIPTION OF THE INVENTION

The compounds of Formulas I–IV are totally synthetic and, therefore, racemic and the racemates may be resolved into their optical isomers. Formula II represents only one isomer of a racemic pair and the mirror image thereof represents the other isomer. Since the 1-carbon atom of the 2,2-dichlorocyclopropyl moiety has two possible spatial configurations, Formulas I, III and IV represent one isomer of each of two racemic pairs and the two possible mirror images represent the other two isomers. The features $$\begin{matrix} C \\ \vdots \\ X \end{matrix}$$

and C..Y of Formulas I–IV represent bonds oriented below the plane of the page if the plane of the tetralin moiety is considered to be in the plane of the page. Thus, X is equatorial and Y is axial with reference to the tetralin moiety and X and Y are cis with reference to each other.

In the N-alkylation of the compounds of Formula II with (2,2-dichlorocyclopropyl)methyl-An in the presence of an acid absorber, -An is the anion of any strong organic or inorganic acid which does not interfere with the alkylation, especially halide, for example, chloride or bromide, or arylsulfonate, for example, p-toluenesulfonate. Any effective acid absorber may be used, especially an alkali metal carbonate, for example, sodium bicarbonate. Ordinarily it is preferable to use a diluent such as a lower alkanol, for example, methanol or ethanol, or an N,N-(di-lower-alkyl)-lower alkanamide, for example, N,N-dimethylformamide or N,N- dimethylacetamide. The N-alkylation may be carried out with or without heating or cooling.

The reduction of the compounds of Formula III with a reagent effective in reducing N-carbonyl to N-methylene and in cleaving the (2,2-dichlorocyclopropyl)carbonyl-oxygen bond without affecting any other part of the molecule is accomplished, for example, with diborane. A diluent is preferably used, for example, ether or tetrahydrofuran. The reduction may be carried out with or without heating or cooling.

The O-demethylation of the compounds of Formula IV with a reagent effective in cleaving the methyl ether bond without affecting any other part of the molecule, for example, boron tribromide. A diluent is preferably used, for example, methylene dichloride. The O-demethylation is usually carried out with cooling and subsequent warming.

The compounds of Formula III are prepared by N-acylation of the corresponding compounds of Formula II with an active acylating form of 2,2-dichlorocyclopropanecarboxylic acid such as an acid halide, for example, the acid chloride, the anhydride or a mixed anhydride, for example, the mixed anhydride with trifluoroacetic acid. The N-acylation may be carried out with or without a diluent, with or without an acid absorber and with or without heating or cooling. The diluent and the acid absorber may be the same, for example, pyridine, or different, for example, chloroform and triethylamine, respectively. N-Acylation may be accompanied by O-acylation of the 8-hydroxyl, but any O-acyl is removed by the subsequent reduction.

The compounds of Formula IV are prepared by N-alkylation or N-acylation-reduction of the corresponding 6-X-11-Y-1,2,3,4,5,6-hexahydro-8-methoxy-2,6-methano-3-benzazocines as described above for the preparation of the compounds of Formula I from the compounds of Formula II.

Some of the compounds of Formula II are known. Those which are not known are prepared by O-demethylation of the corresponding 6-X-11-Y-1,2,3,4,5,6-hexahydro-8-methoxy-2,6-methano-3-benzazocines with, for example, concentrated hydrobromic acid.

Some of the 6-X-11-Y-1,2,3,4,5,6-hexahydro-8-methoxy-2,6-methano-3-benzazocines are known. Those which are not known are prepared by N-demethylation of the corresponding 6-X-11-Y-1,2,3,4,5,6-hexahydro-8-methoxy-3-methyl-2,6-methano-3-benzazocines with, for example, cyanogen bromide, which produces the corresponding 6-X-11-Y-3-cyano-1,2,3,4,5,6-hexahydro-8-methoxy-2,6-methano-3-benzazocines, followed by aqueous hydrochloride acid, by which 3-cyano is removed.

The 6-X-11-Y-1,2,3,4,5,6-hexahydro-8-methoxy-3-methyl-2,6-methano-3-benzazocines are all known and are described by Eddy and May (Synthetic Analgesics, Part IIB of Parts IIA and IIB, Pergamon Press, Oxford, 1966, pp. 117-137), May and co-workers (J. Med. Chem., Vol. 12, No. 2, 1969, pp. 405-408), U.S. Pat. No. 3,320,265 or Netherlands Patent Application No. 73/14758.

The compounds of Formula I are amino bases and react with organic and inorganic acids to form acid addition salts. Due to the presence of the basic amino grouping, the free base forms represented by Formula I react with organic and inorganic acids to form acid addition salts. The acid addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid addition salt is isolated by filtration, if it is insoluble in the reaction medium, or by evaporation of the reaction medium to leave the acid addition salt as a residue. The acid moieties or anions in these salt forms are in themselves neither novel nor critical and therefore can be any acid anion or acid-like substance capable of salt formation with the base.

Representative acids for the formation of the acid addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like. All of the acid addition salts are useful as sources of the free bases by reaction with a stronger base. Thus, if one or more characteristics such as solubility, molecular weight, physical appearance, toxicity or the like of a given base or acid addition salt thereof render that form unsuitable for the purpose at hand, it can be readily converted to another more suitable form. For pharmaceutical purposes, acid addition salts of relatively non-toxic, pharmaceutically acceptable acids, for example, hydrochloric acid, lactic acid, tartaric acid, and the like are of course employed. Either the free bases or the acid addition salts thereof may crystallize as crystalline solvates with solvent of crystallization in integral or fractional amounts.

The following example illustrates the invention. Structures of products are inferred from known structures of starting materials and analogous processes and are confirmed, and purity of starting materials and products is determined, by melting temperature, boiling temperature, elemental analysis, infrared spectral analysis, ultraviolet spectral analysis, nuclear magnetic spectral analysis, mass spectral analysis and/or optical rotational analysis.

EXAMPLE

A. A mixture of 1,2,3,4,5,6-hexahydro-cis-6,11-dimethyl-2,6-methano-2,6-methano-3-benzazocin-8-ol (described as 2'-hydroxy-5,9-dimethyl-6,7-benzomorphan in EXAMPLE 6 of U.S. Pat. No. 3,138,603) (11.2 g.), (2,2-dichlorocyclopropyl)methyl bromide (prepared by cleavage of bis(2,2-dichlorocyclopropyl)-methyl ether with boron tribromide, b.r. 73°–84° C. (mostly 76°–80° C.)/14 mm.)(10.5 g ), sodium bicarbonate (11.2 g.) and N,N-dimethylformamide(70ml.) was stirred under reflux for one hour, then filtered. The filter cake was washed with ethanol and the filtrate was concentrated under vacuum. The residue was extracted with ether. The ether extracts were washed with water, dried, decolorized with charcoal and concentrated under vacuum. Ethereal hydrogen chloride was added to a solution of the residual yellow syrup (14.7 g.) in ether, affording 3-(2,2-dichlorocyclopropyl)methyl-1,2,3,4,5,6-hexahydro-cis-6,11-dimethyl-2,6-methano-3-benzazocin-8-ol hydrochloride as an amorphous white solid mixture of stereoisomers (shrinking temperature, 146° C.; softening temperature, 160° C.; bubbling temperature, 200° C.).

B. Acylation of 1,2,3,4,5,6-hexahydro-cis-6,11-dimethyl-2,6-methano-3-benzazocin-8-ol with 2,2-dichlorocyclopropanecarbonyl chloride affords 3-(2,2-dichlorocyclopropyl)carbonyl- 1,2,3,4,5,6-hexahydro-cis-6,11-dimethyl-2,6-methano-3-benzazocin-8ol possibly mixed with the 8-(2,2-dichlorocyclopropanecarboxylate) ester. Reduction of the mixture with diborane affords 3-(2,2-dichlorocyclopropyl)methyl-1,2,3,4,5,6-hexahydro-cis-6,11-dimethyl-2,6-methano-3-benzazocin-8-ol, the free base form of the product of part A.

C. Alkylation of 1,2,3,4,5,6-hexahydro-cis-6,11-dimethyl-8-methoxy-2,6-methano-3-benzazocine (described as an oil in EXAMPLE 5 of U.S. Pat. No. 3,138,603) with (2,2-dichlorocyclopropyl)-methyl bromide affords 3-(2,2-dichlorocyclopropyl)methyl-1,2,3,4,-5,6-hexahydro-cis-6,11-dimethyl-8-methoxy-2,6-methano-3-benzazocine, O-demethylation of which with boron tribromide affords 3-(dichlorocyclopropyl)methyl-1,2,3,4,5,6-hexahydro-cis-6,11-dimethyl-2,6-methano-3-benzazocin-8-ol, the free base form of the product of part A.

BIOLOGICAL TEST RESULTS

As stated above the compounds of Formula I are useful as strong analgesics and narcotic antagonists.

The test used for narcotic antagonism is the tail-flick test, which is also used to test for narcotic agonism, as follows:

Tail-flick Agonist Test

Rats normally respond to a thermal stimulus applied to the tail by flicking their tails out from under the heat source. The intensity of the stimulus utilized is one which produces control response times (CRT) of 2–4 seconds. Experimental response times (ERT) are determined 30 minutes after subcutaneous injections and 60 minutes after oral medications. The stimulus is terminated if animals do not respond after an exposure of 20 seconds. Therefore, the maximum possible increase (MPI) in response time for any given animal is 20 minus the CRT. The average percent effect, or percent of the maximum possible increase (%MPI) obtained after any given test compound treatment is calculated by the formula $$\% \; MPI = 100 \times \frac{\text{average } ERT - \text{average } CRT}{20 - \text{average } CRT}$$

Test compounds are screened using 6 animals per treatment, usually at doses of 120 milligrams per kilogram subcutaneously or 200 milligrams per kilogram orally. The standard injection volume for test compounds is 1.0 mililiter per kilogram subcutaneously and 10 milliliters per kilogram orally. ED50 or ED80 values of active compounds are obtained by the Miller and Tainter [Proc. Soc. Exptl. Biol., N.Y., 57:261(1944)] method of probit analysis of data from at least 3 dosage levels using 18 animals per treatment.

In the foregoing tail-flick agonist test 3-(2,2-dichlorocyclopropyl)-methyl-1,2,3,4,5,6-hexahydro-cis-6,11-dimethyl-2,6-methano-3-benzazocin-8-ol, the free base of the hydrochloride salt product of part A of the example which was used in the test, was inactive at 120 milligrams per kilogram subcutaneously.

Tail-flick Antagonist Test

The rat tail-flick test is also used to determine whether compounds have narcotic antagonist activity. Animals are pretreated (10 minutes for subcutaneous route, 20 minutes for oral route) with test compound and are then given a standard ED80 dose of phenazocine hydrobromide (0.5 milligrams per kilogram subcutaneously). Active compounds reduce in a dose-dependent manner, and can completely block, the agonist effect of all narcotics. The average percent antagonist effect produced by any given treatment is calculated by the formula $$\% \; \text{antagonism} = 100 - \frac{\% \; MPI \text{ of narcotic } + \text{ test drug}}{0.80}$$

Test compounds are screened using 6 animals per treatment, usually at 80 milligrams per kilogram subcutaneously or 200 milligrams per kilogram orally. The standard injection volume for test compounds is 1.0 milliliter per kilogram subcutaneously and 10 milliliters per kilogram orally. AD50 values of active compounds are obtained from Litchfield-Wilcoxon [J. Pharm. Exptl. Therap., 96:99(1944)] plots of data from at least 3 dosage levels using 18 animals per treatment.

In the foregoing tail-flick antagonist test a subcutaneous AD50 value of 0.36 milligrams per kilogram having 95% confidence limits of 0.26-0.50 was obtained for 3-(2,2-dichlorocyclopropyl)methyl-1,2,3,4,5,6-hexahydro-cis-6,11-dimethyl-2,6-methano-3-benzazocin-8-ol, the free base of the hydrochloride salt product of part A of the example which was used in the test.

As presumptive tests of strong analgesia the anti-acetylcholine writhing test and the anti-phenylquinone writhing test are carried out as follows:

Anti-acetylcholine Writhing Test

An intraperitoneal injection of acetylcholine, 3.2 milligrams per kilogram, causes mice to exhibit a response consisting of abdominal constriction, and sometimes twisting, followed by extension of the hind limbs. This response has also been called writhing. Animals are pretreated with test compounds (20 minutes for both subcutaneous and oral routes) and observed for two minutes immediately following the administration of acetylcholine. Mice not responding during the two-minute observation period are scored protected while those responding one or more times are scored not protected. Test compounds are screened at doses of 75 and 25 milligrams per kilogram subcutaneously or 150 and 50 milligrams per kilogram orally. The standard injection volume for test compounds is 10 milligrams per kilogram. ED50 values for active compounds are estimated by probit analysis of quantal scores for 4 or more dosage levels using 15 animals per dose. Vehicle-pretreated control animals are tested concurrently with each run of 15 experimental animals.

In the foregoing anti-acetylcholine writhing test a subcutaneous ED50 value of 0.5 milligrams per kilogram having 95% confidence limits of 0.2-0.9 and an oral ED50 value of 7.1 milligrams per kilogram having 95% confidence limits of 3.7-13 were obtained for 3-(2,2-dichlorocyclopropyl)methyl-1,2,3,4,5,6-hexahydro-cis-6,11-dimethyl-2,6-methano-3-benzazocin-8-ol, the free base of the hydrochloride salt product of part A of the example which was used in the test.

Anti-phenylquinone Writhing Test

The ability of compounds to prevent phenyl-p-quinone (phenylquinone) induced writhing in mice is determined in this test. An intraperitoneal injection of phenylquinone, 3.0 milligrams per kilogram, causes mice to exhibit the same writhing response as does acetylcholine as described above. Animals are pretreated with test compounds (15 minutes for subcutaneous route, 30 minutes for oral route) and observed for three one-minute intervals during the 5-12 minutes following administration. Mice responding fewer than three times during the three one-minute observation periods are scored protected while those responding three or more times are scored not protected. Test compounds are screened using 10-14 animals per treatment, usually at doses of 75-100 milligrams per kilograms subcutaneously or 150-200 milligrams per kilogram orally. The standard injection volume for test compounds is 10 milligrams per kilogram. ED50 values for active compounds are estimated by probit analysis of quantal scores for 3-5 dosage levels using 14-30 animals per dose. Vehicle-pretreated control animals are tested daily.

In the foregoing anti-phenylquinone writhing test a subcutaneous ED50 value of 0.78 milligrams per kilogram having 95% confidence limits of 0.17-1.6 was obtained for 3-(2,2-dichlorocyclopropyl)-methyl-1,2,3,4,5,6-hexahydro-cis-6,11-dimethyl-2,6-methano-3-benzazocin-8-ol, the free base of the hydrochloride salt product of part A of the example which was used in the test. The compound was also active orally, but the data were insufficient to estimate an ED50 value.

I claim:
1. 6-X-11-Y-3-(2,2-Dichlorocyclopropyl)methyl-1,2,3,4,5,6-hexahydro-2,6-methano-3-benzazocin-8-ol having the structural formula

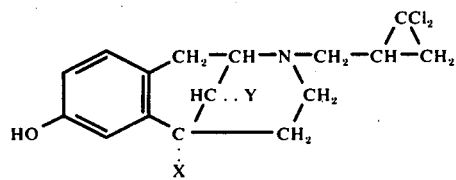

wherein
X is hydrogen, methyl, ethyl, propyl, allyl or phenyl and Y is hydrogen, methyl or ethyl or an acid addition salt thereof.
2. 3-(2,2-Dichlorocyclopropyl)methyl-1,2,3,4,5,6-hexahydro-cis-6,11-dimethyl-2,6-methano-3-benzazocin-8-ol or an acid addition salt thereof.

* * * * *